(12) United States Patent
Udell et al.

(10) Patent No.: US 7,060,263 B2
(45) Date of Patent: Jun. 13, 2006

(54) SUPER ABSORPTION COENZYME $Q_{10}$

(76) Inventors: Ronald G. Udell, 527 Hillgreen Dr., Beverly Hills, CA (US) 90212; Siva P. Hari, 3407 Sunnyside Dr., Riverside, CA (US) 92506

( * ) Notice: Subject to any disclaimer, the term of this patent is extended or adjusted under 35 U.S.C. 154(b) by 268 days.

(21) Appl. No.: 10/640,868

(22) Filed: Aug. 14, 2003

(65) Prior Publication Data

US 2004/0071682 A1    Apr. 15, 2004

Related U.S. Application Data

(62) Division of application No. 09/887,874, filed on Jun. 22, 2001, now Pat. No. 6,623,734.

(60) Provisional application No. 60/213,337, filed on Jun. 22, 2000.

(51) Int. Cl.
| | |
|---|---|
| *A61K 38/43* | (2006.01) |
| *A61K 47/00* | (2006.01) |
| *A61K 9/14* | (2006.01) |
| *A61K 9/48* | (2006.01) |
| *A61K 9/50* | (2006.01) |
| *A61K 31/075* | (2006.01) |
| *A61K 31/355* | (2006.01) |
| *A01N 25/28* | (2006.01) |

(52) U.S. Cl. .................... 424/94.1; 424/439; 424/451; 424/456; 424/458; 424/489; 424/498; 424/502; 514/458; 514/725; 514/787; 514/944; 514/962

(58) Field of Classification Search ............... 424/94.1, 424/439, 451, 456, 458, 415, 489, 498, 502; 514/458, 725, 787, 944, 962
See application file for complete search history.

(56) References Cited

U.S. PATENT DOCUMENTS

| | | | |
|---|---|---|---|
| 4,824,669 | A | 4/1989 | Folkers et al. |
| 5,500,416 | A | 3/1996 | Miyazawa et al. |
| 5,532,002 | A | 7/1996 | Story |
| 5,891,469 | A | 4/1999 | Amselem |
| 6,020,383 | A | 2/2000 | Stone et al. |
| 6,054,136 | A | 4/2000 | Farah et al. |
| 6,069,167 | A | 5/2000 | Sokol |
| 6,203,818 | B1 | 3/2001 | Vester |
| 6,365,181 | B1 * | 4/2002 | Matthews .................... 424/451 |
| 6,545,184 | B1 | 4/2003 | Lipshutz |
| 6,616,942 | B1 | 9/2003 | Udel |
| 6,782,307 | B1 * | 8/2004 | Wilmott et al. ............. 700/233 |

FOREIGN PATENT DOCUMENTS

| | | |
|---|---|---|
| DE | 3512054 | 10/1986 |
| EP | 0 888 774 | 1/1999 |

OTHER PUBLICATIONS

R. Chopra et al, "A New Coenzyme Q10 Preparation with Enhanced Bioavailability", FASEB Journal, 11 (3), pp. A586, 1997, Abstract.

M. Weis, et al., "Bioavailability of Four Oral Coenzyme Q10 Formulations in Healthy Volunteers", Molec. Aspects. Med., vol. 15, (Supplement) pp. s273-s280, 1994.

http://www.pformulate.com/pformsoftgel.htm.

* cited by examiner

*Primary Examiner*—Ralph Gitomer
*Assistant Examiner*—Kailash C. Srivastava
(74) *Attorney, Agent, or Firm*—Dorsey & Whitney LLP; Scott D. Rothenberger

(57) ABSTRACT

An improved soft gelatin formulation and process methodology that increases single Coenzyme $Q_{10}$ molecules presented to the absorption channels of the small intestines by providing medium chain triglycerides, Vitamin E and natural beta carotene to Coenzyme $Q_{10}$ in a soft gel capsule to increase the absorption thereof.

3 Claims, No Drawings

SUPER ABSORPTION COENZYME $Q_{10}$

CROSS REFERENCE TO RELATED APPLICATIONS

This application claims priority of U.S. application Ser. No. 09/887,874, filed on Jun. 22, 2001 now U.S. Pat. No. 6,623,734 which claims priority from U.S. Provisional Application Ser. No. 60/213,337, filed Jun. 22, 2000, the contents of which are herein incorporated by reference.

FIELD OF THE INVENTION

This invention relates to an important improved soft gelatin formulation and process methodology that increases single Coenzyme $Q_{10}$ molecules presented to the absorption channels of the small intestines.

BACKGROUND OF THE INVENTION

Coenzyme $Q_{10}$ ($CoQ_{10}$) is a large molecular weight lipid compound that is produced in the liver and other organs. The total human body content is 1.4 to 1.8 grams depending on the individual's age and fitness level. $CoQ_{10}$ is found in all tissues of the body. It is mostly concentrated in the mitochondria and other organelles that help the body metabolize nutrients into energy. These include organs with high levels of metabolic activity. Organs, whose primary purpose is energy production, tend to store and use $CoQ_{10}$ in large amounts. Such organs include the heart, liver, and skeletal muscle tissue. The heart and skeletal muscle of an aaverage human contain about 1000 mg of $CoQ_{10}$. This is in contrast to metabolically inactive body components such as the blood, which only contains about 4 mg of $CoQ_{10}$ However, blood plays an important role in as a $CoQ_{10}$ reservoir. Blood helps to transport $CoQ_{10}$ from endogenous $CoQ_{10}$ made in the liver and exogenous $CoQ_{10}$ absorbed from digested food in the intestinal tract. Endogenous $CoQ_{10}$ accounts for approximately 56 percent of the body's supply. The remaining 44 percent must be provided through diet and supplementation. These numbers are currently being studied but the latest studies indicate lower endogenous production of $CoQ_{10}$, which indicates a significant deficiency, in correlation with increased age. Furthermore, certain disease states such as cardio myopathy and high cholesterol levels, which are treated with Statin drugs, seem to deplete endogenous $CoQ_{10}$ production thereby indicating a need for supplementation. These deficiencies in the nutrient have no relation to daily caloric intake but are indicative of poor vitamin absorption from ingested foods. The body requires the addition of vitamins to aid in the endogenous production of $CoQ_{10}$; in particular, the B Vitamins play a crucial role in this synthesis.

The human body's need for $CoQ_{10}$ varies between individuals. Factors that affect this are age, physical activity, and health. The body uses an estimated 5 to 9 mg per day of $CoQ_{10}$. This nutrient is essential for life because it is important in the synthesis of energy. The vast majority of energy synthesis occurs in the mitochondria of cells. Here $CoQ_{10}$ primarily functions as an electron carrier in the Electron Transport Chain where Adenosine Triphosphate (ATP) is synthesized. $CoQ_{10}$ donates an electron during ATP synthesis and is subsequently oxidized. $CoQ_{10}$ also can function as an antioxidant during synthesis where oxidation removes its electron making it non-functional for use in ATP synthesis.

Conditions of high metabolic stress deplete the body's endogenous supply of $CoQ_{10}$. Because of this, $CoQ_{10}$ supplementation becomes necessary to meet the body's requirement for energy production. Under these conditions, dietary supplementation is shown effective provided that the nutrient is delivered in an ideal form. An improved soft gelatin formulation and process of $CoQ_{10}$ soft gel manufacturing has been used to improve conditions associated with heart failure, chronic fatigue, and for patients with psoriasis and plantar warts. In all of these, an improved soft gelatin formula has been clinically proven, at doses of 30–100 mg/day, to be superior to 60 mg/day dry capsules and previoously available 100 mg/day soft gel formulas.

Research has had difficulty ascertaining the appropriate $CoQ_{10}$ dose for a diseased individual in comparison to a normal individual. However, the normally recommended dose of 10 to 30 mg/day has been found to be ineffective for individuals with significant deficiencies. For the past 15 years, it has become accepted that poor intestinal absorption of certain forms of $CoQ_{10}$ limits the effectiveness of its use. Because of this, dosages of 50 mg, 100 mg and even 150 mg are commercially available to the consumer, but at a considerable expense. This deters many persons from supplementing their diets with sufficient $CoQ_{10}$, a fact that can have deleterious health effects.

Folkers et al. (U.S. Pat. No. 4,824.669) addresses a soft gel capsule with $CoQ_{10}$ and at least one vegetable oil carrier. This formula was found to increase blood basal levels of $CoQ_{10}$ to 2.5 g/ml in comparison to 1.6 g/ml from an equivalent 100 mg dose of a dry powder formulation. While many different $CoQ_{10}$ formulas claim increased intestinal absorption of the nutrient, the data supporting these claims are often inconclusive.

It is clear that a far more efficient formula will produce better results with less $CoQ_{10}$ than traditional soft gel or dry formulations.

SUMMARY OF THE INVENTION

The present invention is made from a stable, non-toxic soft gelatin Coenzyme formulation. The process methodology of Coenzyme $Q_{10}$, which increases Coenzyme$Q_{10}$, levels in the intestinal tract and subsequently, in the energy producing organs of the body through carriage in the blood stream. The preferred soft gel formula includes: Coenzyme $Q_{10}$; medium chain triglycerides or GelOil SC; Vitamin E as mixed tocopherols, which also act as an added antioxidant; Rice Bran Oil; Yellow Beeswax; and Natural Beta carotene. The medium chain triglycerides or GelOil SC work as carriers and serve to increase the bioavailability of the $CoQ_{10}$ in the gut for a superior absorption formula. The formula need only be administered only twice per day as such is found to be effective and serves the added benefit of reducing the cost to the consumer and ease of use.

The medium chain triglycerides can be replaced with GelOil SC, which is a wetting and suspension agent, those functions in a like manner as the more expensive medium chain triglycerides. GelOil SC is composed of refined soybean oil (CAS# 8001-22-7), mixed composition of mono-, di-, tri-glycerides of a 16 to 18 carbon chain length, and polyglycerol oleate (CAS# 9007-48-1). The replacement of the medium chain triglycerides with GelOil SC provides comparable if not better solubility in the intestines and is also a cost effective alternative to the formula, an added benefit to the consumer.

To achieve increased intestinal absorption of $CoQ_{10}$, the present formulation contains refined soybean oil (Gel Oil SC) or medium chain triglycerides to improve the solubility of the product and provide superior absorption in the intestinal tract. The large molecule oil carriers in the invention allows for superior solubility of the product, which results in greater absorption. Superior absorption of any nutrient is determined by kinetics. The primary carrier used in this invention medium chain triglycerides, or GelOil SC help the large molecule that is $CoQ_{10}$ improve its absorption kinetics. This is possible because the appropriate carrier can increase the number of single molecules presented to lacteal pores of the intestines into the lymphatic system. The carrier used presents a greater number of molecules that can overcome the three barriers to absorption. The barriers are molecular size, concentration gradient, and membrane thickness. Membrane thickness is sometimes impaired in the elderly through disease states, but this should not affect the availability of $CoQ_{10}$ in the system. Medium chain triglycerides and GelOil SC are superior to large chain triglycerides. This is because they do not limit the number of single $CoQ_{10}$ molecules available for absorption through the lacteals. Therefore, using either of these carriers improves the number of single $CoQ_{10}$ molecules in the intestines. Research has shown that the greater the number of single molecules of CoQ10, the better the chances for improved absorption.

Kishi et al., refers to this when they qualify that the ten isoprenoid units found in $CoQ_{10}$ make it an extremely water insoluble. However, $CoQ_{10}$ is a highly lipophilic molecule. They confirm that the bioavailability of the molecule is related directly to its dissolution rate, which the current invention maximizes. The physical chemistry of $CoQ_{10}$ must be taken into consideration in any formulation, which claims improved absorption. Here, the addition of medium chain triglycerides or GelOil makes this formula extremely bioavailable because it satisfies the molecules lipophilic attraction. This is thought to lead to enhanced absorption potential.

It is therefore an object of the present invention to provide an improved soft gel formulation of $CoQ_{10}$ and a methodology of processing such that produces a form with significantly greater absorption than prior soft or dry formulations.

Another object is to reduce the cost of providing an effective level of in a human body, whether normal or diseased.

Another object is to provide a soft gel producing process that provides a maximum amount of into the blood stream.

It is the further object of the present invention to provide a soft gel formula and methodology of administration that produces greater absorption in the intestine, which benefits the individual, both in nutrition and cost.

These and other objects and advantages will become apparent to those skilled in the art after considering the following detailed description of the invention.

DETAILED DESCRIPTION OF THE PREFERRED EMBODIMENTS

The novelty of the formulation involves the following sequence of ingredients and process methodology.

1. All ingredients must be mixed under a nitrogen blanket and maintain throughout blending;

2. Melt Beeswax in Rice Bran Oil, Soybean oil, and Medium Chain Triglycerides, heat mixture to a minimum of 60 degrees Celsius;

3. Allow mixture to cool to at least 30 degrees Celsius and add Vitamin E and natural Beta Carotene;

4. When temperature is below 26 degrees Celsius, add Coenzyme Q10, at no time should the mixture be allowed to exceed 26 degrees Celsius after the Coenzyme Q10 is added;

5. Mix for a minimum of 30 minutes to assure the mixture is homogenous and that no air remains; and 6. Encapsulate in a gel capsule.

When the medium chain triglycerides are replaced with GelOil SC, the process can eliminate the warming step. This benefits the $CoQ_{10}$ molecule, which is very sensitive to elevated tempertures.

Typical fill amounts in a 400 mg fill of a soft gel capsule which also includes optional 3260 IU of Vitamin A are about as follows:

| | |
|---|---|
| $CoQ_{10}$ | 50–55 mg |
| Yellow Beeswax | 10–15 mg |
| Rice Bran Oil | 40–45 mg |
| Soybean oil | 50–55 mg |
| Medium Chain Triglycerides | 80–85 mg |
| Vitamin E (70% mixed tocopherols) | 150 mg |
| natural Beta Carotene or | 1.9–10 mg |
| $CoQ_{10}$ | 50–55 mg |
| Yellow Beeswax | 10–15 mg |
| Rice Bran Oil | 40–45 mg |
| Soybean oil | 20–25 mg |
| GelOil SC | 110–120 mg |
| Vitamin E (70% mixed tocopherols) | 150 mg |
| natural Beta Carotene | 1.9–10 mg |

Yellow beeswax, rice bran oil, soybean oil and medium chain triglycerides all act as suspending agents while medium chain triglycerides or GelOil SC increase the solubility of $CoQ_{10}$ in the blood. The peak and steady basal absorption characteristics of a dry powder $CoQ_{10}$ product compared to that of the present invention was determined in 16 normal volunteers (20–55 years) in a randomized double blind placebo controlled cross over study design. $CoQ_{10}$ in plasma was measured using hexane extraction and the HPLC method. The product forms were ingested a single and daily 100 mg doses at 7:00 AM. Peak absorption characteristics were determined from a serial blood samples collected before and during supplementation on days −10, 0, 7, 14, 21, and 28 at 7:00 AM while in a fasting state. Control plasma $CoQ_{10}$ levels were similar for all product studies and were not significantly different between studies. the peak absorption time was between 5 and 6 hours and not significantly different between studies. Peak absorption of $CoQ_{10}$ for the powdered $CoQ_{10}$ form was 1.41±0.31 µg/ml while peak absorption of $CoQ_{10}$ for the product of the present invention was 3.64±0.86 µg/ml. In the 28 day steady state study, plasma $CoQ_{10}$ increased rapidly in the first 7–14 days and then gradually increased thereafter in all product forms. The study along with ones with $CoQ_{10}$ in other lipids showed that the greater the number of single $CoQ_{10}$ molecules, the greater the peak and steady state absorption.

The bioavailability of intestinal absorption of $CoQ_{10}$ has been a major controversy in the international research community. However, it is an accepted fact that only 1 to 3 percent of dry powder $CoQ_{10}$ formulation is absorbed through the lacteals in the intestines. Dry powder formulas appear in the blood in a twelve-hour interval. In general, blood levels of 1.2 to 1.6 g/ml have been reported when taking 30 to 60 mg/day of a dry powder formula for 30 days. It has been noted that when a dry powder $CoQ_{10}$ is taken with a fat such as peanut butter, steady-state blood levels of 2.0 to 2.8 g/ml are measurable in the blood. Multiple clinical trials conducted in the United States and Europe using Folkers (U.S. Pat. No. 4,824,669) soft gel. With a dosage of 100 mg/day, multiple investigators have reported blood levels of $CoQ_{10}$ to rise to 2.3 to 3.5 g/ml depending on the laboratory conducting the measurement. The research behind this data is taken from the remaining amount of $CoQ_{10}$ in the blood after an elapsed period of time. Usually this is measured in twelve-hour period for dry formulas but can be determined in 6 hours for soft gelatin suspension formulations further indicating the increased efficiency of a soft gel product.

This is important because a dosage of 50 to 100 milligrams of $CoQ_{10}$ in a soft gelatin formula provides the sedentary individual with the daily $CoQ_{10}$ requirement. It would take at least three of the dry powder capsules at 30 milligrams to produce the same effect as one soft gelatin capsule and six to produce the same effect as two 30 mg soft gel capsules, with the added negative of less single molecules available for presentation to the lacteals in the dry powder form.

The significantly higher absorption levels of soft gelatin formulas results in a 273% greater absorption rate which is established in clinical studies. This further confirms that soft gelatin with the proper oil carriers are superior to dry powder formulas. This fact is crucial for those individuals who have high requirements for $CoQ_{10}$ due to high physical activity or disease.

What is claimed:

1. A method for basel absorption of orally administered $CoQ_{10}$ comprising the step of:
   administering to an individual a composition comprising $CoQ_{10}$, rice bran oil, a mixture of mono-, di- and tri-glycerides of 16 to 18 carbon chain length and polyglycerol oleate, yellow beeswax, soybean oil, vitamin E and Beta carotene.

2. The method as defined in claim 1, wherein said $CoQ_{10}$ composition is supplied in a soft gel capsule.

3. The method as defined in claim 2, wherein said soft gel capsule further comprises:
   Vitamin A.

* * * * *